United States Patent
Bui et al.

(10) Patent No.: US 9,089,503 B2
(45) Date of Patent: **\*Jul. 28, 2015**

(54) COMFORTABLE TRANSFER-RESISTANT COLORED COSMETIC COMPOSITIONS CONTAINING A SILSESQUIOXANE WAX

(75) Inventors: Hy Si Bui, Piscataway, NJ (US); Susan Halpern, Paramus, NJ (US); Mohamed Kanji, Edison, NJ (US)

(73) Assignee: L'OREAL (FR)

( * ) Notice: Subject to any disclaimer, the term of this patent is extended or adjusted under 35 U.S.C. 154(b) by 1230 days.

This patent is subject to a terminal disclaimer.

(21) Appl. No.: 12/131,256

(22) Filed: Jun. 2, 2008

(65) Prior Publication Data

US 2008/0305061 A1 Dec. 11, 2008

Related U.S. Application Data

(60) Provisional application No. 60/942,344, filed on Jun. 6, 2007.

(51) Int. Cl.
| | | |
|---|---|---|
| *A61K 8/89* | (2006.01) | |
| *A61K 8/891* | (2006.01) | |
| *A61K 8/894* | (2006.01) | |
| *A61K 8/895* | (2006.01) | |
| *A61Q 1/02* | (2006.01) | |

(52) U.S. Cl.
CPC . *A61K 8/894* (2013.01); *A61K 8/89* (2013.01); *A61K 8/891* (2013.01); *A61K 8/895* (2013.01); *A61Q 1/02* (2013.01); *A61K 2800/594* (2013.01)

(58) Field of Classification Search
CPC ............ A61Q 1/02; A61K 8/89; A61K 8/894
See application file for complete search history.

(56) References Cited

U.S. PATENT DOCUMENTS

| | | | |
|---|---|---|---|
| 5,492,945 A | 2/1996 | Morita et al. | |
| 5,538,793 A | 7/1996 | Inokuchi et al. | |
| 5,756,568 A | 5/1998 | Morita et al. | |
| 5,783,657 A | 7/1998 | Pavlin et al. | |
| 5,945,471 A | 8/1999 | Morita et al. | |
| 6,268,466 B1 | 7/2001 | MacQueen et al. | |
| 6,280,748 B1 | 8/2001 | Morita et al. | |
| 6,376,078 B1 | 4/2002 | Inokuchi | |
| 6,402,408 B1 | 6/2002 | Ferrari | |
| 6,517,818 B1 | 2/2003 | Golz-Berner et al. | |
| 6,552,160 B2 | 4/2003 | Pavlin | |
| 7,127,280 B2 | 10/2006 | Dauga | |
| 2003/0077240 A1 | 4/2003 | LeGrow et al. | |
| 2004/0156806 A1 | 8/2004 | Patil et al. | |
| 2004/0180011 A1 | 9/2004 | Schlosser | |
| 2005/0180931 A1 | 8/2005 | Oguchi et al. | |
| 2005/0220728 A1* | 10/2005 | Kanji et al. | 424/59 |
| 2006/0013839 A1 | 1/2006 | Yu | |
| 2006/0110347 A1 | 5/2006 | Lu et al. | |
| 2006/0120983 A1 | 6/2006 | Blin et al. | |
| 2006/0292096 A1* | 12/2006 | Yu | 424/64 |
| 2007/0093619 A1 | 4/2007 | Bui et al. | |
| 2007/0142521 A1 | 6/2007 | Brahms et al. | |
| 2007/0149703 A1 | 6/2007 | Caprasse et al. | |
| 2008/0305062 A1 | 12/2008 | Bui et al. | |
| 2008/0305064 A1 | 12/2008 | Bui et al. | |
| 2008/0305067 A1 | 12/2008 | Bui et al. | |

FOREIGN PATENT DOCUMENTS

| | | |
|---|---|---|
| CN | 1823711 A | 8/2006 |
| EP | 0848029 A2 | 6/1998 |
| EP | 0963751 A2 | 12/1999 |
| JP | 06-011684 | 1/1994 |
| JP | 10-176059 | 6/1998 |
| JP | 2000063225 A | 2/2000 |
| JP | 2006-526019 A | 11/2006 |
| JP | 2010-513540 A | 4/2010 |
| JP | 2010-513541 A | 4/2010 |
| WO | 2004103323 A1 | 12/2004 |
| WO | WO 2005/090444 | 9/2005 |
| WO | WO 2005/100444 | 10/2005 |
| WO | 2005105031 A1 | 11/2005 |
| WO | 2008079478 A1 | 7/2008 |
| WO | 2008079479 A2 | 7/2008 |

OTHER PUBLICATIONS

Factsheet—Dow Corning 670 Fluid—Intellectual Property Statement—Apr. 14, 2005.
Virginie Caprasse, Isabelle Van Reeth, Dow Corning S.A., Research Disclosure, A new silicone resin for personal care applications, Research Disclosure Database No. 486008, Published in Oct. 2004 (Electronic publication date: Sep. 10, 2004), Research Disclosure Journal, Kenneth Mason Publications Ltd., The Book Barn, Westbourne, Hants. P010 8RS UK.
CTFA Dictionary, International Cosmetic Ingredient Dictionary (6th edition, 1995), published by The Cosmetic, Toiletry, and Fragrance Association, 1101 17th Street, N.W., Suite 300, Washington, DC 20036-4702.
Co-pending U.S. Appl. No. 11/584,994—Title: Compositions having enhanced cosmetic properties—filed Oct. 23, 2006.

(Continued)

*Primary Examiner* — Rachael E Bredefeld
(74) *Attorney, Agent, or Firm* — Lerner, David, Littenberg, Krumholz & Mentlik, LLP

(57) ABSTRACT

The present invention is directed to a composition containing: (a) at least one propylsilsesquioxane wax substituted with alkyl units having at least 30 carbons; (b) a liquid fatty phase; (c) at least one emulsifier chosen from an emulsifying silicone elastomer; (d) at least one colorant; (e) water; and (f) optionally, at least one film forming resin chosen from a propylphenylsilsesquioxane resin having a molecular weight of from about 2,000 to about 30,000 and comprising at least about 70 mole % propyl siloxy units, based on the total mole % siloxy units of the resin, and at most about 30 mole % phenyl siloxy units, based on the total mole % siloxy units of the resin, and a silicone acrylate copolymer resin. Also disclosed is a method of making up skin involving applying the above described composition onto the skin.

28 Claims, No Drawings

(56) References Cited

OTHER PUBLICATIONS

"Dow Corning 670 Fluid," Product Information: Personal Care, Ref. No. 27/1158-01 (2004).

"Personal Care Applications for Silsesquioxane Resin Wax", ip.com Journal, ip.com Inc., West Henrietta, NY, US, Dec. 8, 2005, XP013112049.

"Sucrose acetate isobutyrate," pubchem, NCBI, accessed Oct. 1, 2013, pp. 1-5.

Chinese Office Action for Application No. 200810142893.8 dated Jun. 25, 2013.

Extended European Search Report for Application No. 08251967.9 dated Mar. 12, 2014.

Hidetoshi Kondo, "Cross-linked-Type Silicone Emulsifiers—Emulsifying Properties Thereof and Application Thereof in Cosmetics", Fragrance Journal, Jun. 2002, pp. 68 to 74.

Japanese Office Action for Application No. 2008-148499 dated Feb. 17, 2014.

Extended European Search Report for Application No. EP08251968 dated Mar. 18, 2014.

Mintel; Apr. 2007, "Mousse Foundation", XP002720910, Database accession No. 685829, Abstract.

Mintel, Apr. 2007, "Avon Glazewear Lipstick", <http:/gnpd.com>.

Third Party Observations for JP2013-243016 dated May 9, 2014.

\* cited by examiner

COMFORTABLE TRANSFER-RESISTANT COLORED COSMETIC COMPOSITIONS CONTAINING A SILSESQUIOXANE WAX This application is based on and claims the benefit of U.S. Provisional Application Ser. No. 60/942,344, entitled COMFORTABLE, TRANSFER-RESISTANT COLORED COSMETIC COMPOSITIONS CONTAINING A SILSESQUIOXANE WAX, filed Jun. 6, 2007, the entire disclosure of which is incorporated by reference herein.

BACKGROUND OF THE INVENTION

Cosmetic compositions used to make up a user's skin must be able to impart color with little or no transfer. They must also provide good wear properties. The transfer resistance and wear of cosmetic compositions are usually obtained through the use of film forming resins such as silicone film forming resins. While the use of silicone film forming resins in colored cosmetics is popular, one drawback associated with their use is that they tend to be brittle and flake off. This phenomenon results in the need to use a plasticizer, in combination with the resin, in order to render the resultant film more flexible and, hence, less susceptible to flake off and poor transfer resistance. Moreover, the resultant films formed by the resins are uncomfortable on human skin.

Therefore, it is an object of the present invention to provide a method and composition for making up skin in a manner which delivers a combination of transfer resistance, superior comfort and feel. It is also an object of the present invention to provide a composition which is stable.

BRIEF SUMMARY OF THE INVENTION

One aspect of the present invention is directed to a composition containing: (a) at least one propylsilsesquioxane wax substituted with alkyl units having at least 30 carbons; (b) a liquid fatty phase; (c) at least one emulsifier chosen from an emulsifying silicone elastomer; (d) at least one colorant; (e) water; and (f) optionally, at least one film forming resin chosen from a propylphenylsilsesquioxane resin having a molecular weight of from about 2,000 to about 30,000 and comprising at least about 70 mole % propyl siloxy units, based on the total mole % siloxy units of the resin, and at most about 30 mole % phenyl siloxy units, based on the total mole % siloxy units of the resin, and a silicone acrylate copolymer resin.

Another aspect of the present invention is directed to method of making up skin involving applying onto the skin the above-disclosed composition.

It has been surprisingly discovered that the above-described cosmetic composition is stable, has a unique texture, and provides transfer resistance and superior comfort.

DETAILED DESCRIPTION OF THE INVENTION

Other than in the operating examples, or where otherwise indicated, all numbers expressing quantities of ingredients and/or reaction conditions are to be understood as being modified in all instances by the term "about".

Propylsequioxane Waxes Substituted with Alkyl Units having at Least 30 Carbons

The cosmetic compositions of the present invention comprise a propylsilsesquioxane wax substituted with alkyl units having at least 30 carbons.

Propylsilsesquioxane waxes, in general, have been disclosed in patent publication WO2005/100444, published on Oct. 27, 2005, the entire content of which is hereby incorporated by reference.

It should be noted, however, that not all propylsilsesquioxane waxes yield stable colored cosmetic emulsion products. More particularly, it has been found that only those propylsilsesquioxane waxes substituted with alkyl units having at least 30 carbons are stable.

The propylsilsesquioxane wax comprises at least 40 mole % of siloxy units having the formula $(R_2R'SiO_{1/2})_x(C_3H_7SiO_{3/2})_y$, where x and y have a value of 0.05 to 0.95, R is an alkyl group having from 1 to 8 carbon atoms, and R' is a monovalent hydrocarbon having 30 to 40 carbon atoms and greater. As used herein, x and y represent the mole fraction of $(R_2R'SiO_{1/2})$ and $(C_3H_7SiO_{3/2})$ siloxy units relative to each other present in the propylsilsesquioxane wax. Thus, the mole fraction of $(R_2R'SiO_{1/2})$ and $(C_3H_7SiO_{3/2})$ siloxy units each can independently vary from 0.05 to 0.95. Preferably R is a methyl, and R' is an alkyl having at least 30 carbons, available from Dow Corning.

Typically, the value of x is 0.05 to 0.95, or alternatively, 0.2 to 0.8, the value of y is 0.05 to 0.95, alternatively 0.2 to 0.8. However, the combination of $(R_2R'SiO_{1/2})$ and $(C_3H_7SiO_{3/2})$ siloxy units present must total at least 40 mole %, alternatively 60 mole %, or alternatively 90 mole % of all siloxy units present in the propylsilsesquioxane wax.

The number average molecular weight of the propylsilsesquioxane wax substituted with alkyl units having at least 30 carbons typically ranges from about 750 to about 10,000, such as from about 1,000 to about 5,000.

The propylsilsesquioxane wax substituted with alkyl units having at least 30 carbons is generally present in the cosmetic composition of the present invention in an amount ranging from about 0.5% to about 40% by weight; such as from about 1% to about 30% by weight; such as from about 2% to about 20% by weight, such as from about 3% to about 10% by weight, all weights being based on the weight of the composition as a whole.

Liquid Fatty Phase

The cosmetic compositions of the present invention comprise a liquid fatty phase. The liquid fatty phase may comprise at least one volatile oil such as a volatile silicone oil, a volatile non-silicone oil, and/or at least one non-volatile oil such as a non-volatile silicone oil or a non-volatile non-silicone oil.

In one embodiment, the compositions of the present invention are substantially free of volatile silicone oils (i.e., contain less than about 0.1% volatile silicone oils). In another embodiment, the compositions are substantially free of volatile non-silicone oils (i.e., contain less than about 0.1% volatile non-silicone oils). In another embodiment, the compositions are substantially free of non-volatile oils (i.e., contain less than about 0.1% non-volatile oils). In another embodiment, the liquid phase comprises hydrocarbon based oils such as hydrocarbon oils, alcohols, esters and ethers.

Suitable volatile silicone oils include, but are not limited to, linear or cyclic silicone oils having a viscosity at room temperature less than or equal to 6cSt and having from 2 to 7 silicon atoms, these silicones being optionally substituted with alkyl or alkoxy groups of 1 to 10 carbon atoms. Specific oils that may be used in the invention include octamethyltetrasiloxane, decamethylcyclopentasiloxane, dodecamethylcyclohexasiloxane, heptamethyloctyltrisiloxane, hexamethyldisiloxane, decamethyltetrasiloxane, dodecamethylpentasiloxane and their mixtures. Other volatile oils which may be used include KF 96A of 6 cSt viscosity, a commercial product from Shin Etsu having a flash point of 94° C. Preferably, the volatile silicone oils have a flash point of at least 40° C.

Non-limiting examples of volatile silicone oils are listed in Table 1 below.

TABLE 1

| Compound | Flash Point (° C.) | Viscosity (cSt) |
| --- | --- | --- |
| Octyltrimethicone | 93 | 1.2 |
| Hexyltrimethicone | 79 | 1.2 |
| Decamethylcyclopentasiloxane (cyclopentasiloxane or D5) | 72 | 4.2 |
| Octamethylcyclotetrasiloxane (cyclotetradimethylsiloxane or D4) | 55 | 2.5 |
| Dodecamethylcyclohexasiloxane (D6) | 93 | 7 |
| Decamethyltetrasiloxane (L4) | 63 | 1.7 |
| KF-96 A from Shin Etsu | 94 | 6 |
| PDMS (polydimethylsiloxane) DC 200 (1.5 cSt) from Dow Corning | 56 | 1.5 |
| PDMS DC 200 (2 cSt) from Dow Corning | 87 | 2 |
| PDMS DC 200 (5 cSt) from Dow Corning | 134 | 5 |
| PDMS DC 200 (3 St) from Dow Corning | 102 | 3 |

Suitable volatile non-silicone oils may be selected from volatile hydrocarbon oils, alcohols, volatile esters and volatile ethers. Examples of such volatile non-silicone oils include, but are not limited to, volatile hydrocarbon oils having from 8 to 16 carbon atoms and their mixtures and in particular branched $C_8$ to $C_{16}$ alkanes such as $C_8$ to $C_{16}$ isoalkanes (also known as isoparaffins), isododecane, isodecane, isohexadecane, and for example, the oils sold under the trade names of Isopar or Permethyl, the $C_8$ to $C_{16}$ branched esters such as isohexyl or isodecyl neopentanoate and their mixtures. Preferably, the volatile non-silicone oils have a flash point of at least 40° C.

Non-limiting examples of volatile non-silicone oils are listed in Table 2 below.

TABLE 2

| Compound | Flash Point (° C.) |
| --- | --- |
| Isododecane | 43 |
| Isohexadecane | 102 |
| Isodecyl Neopentanoate | 118 |
| Propylene glycol n-butyl ether | 60 |
| Ethyl 3-ethoxypropionate | 58 |
| Propylene glycol methylether acetate | 46 |
| Isopar L (isoparaffin $C_{11}$-$C_{13}$) | 62 |
| Isopar H (isoparaffin $C_{11}$-$C_{12}$) | 56 |

Examples of non-volatile oils that may be used in the present invention include non-volatile silicone oils such as linear polydimethylsiloxanes (PDMSs), that are liquid at room temperature; polydimethylsiloxanes comprising alkyl, alkoxy or phenyl groups, which are pendent and/or at the end of a silicone chain, these groups each containing from 2 to 24 carbon atoms; phenylsilicones, for instance phenyl trimethicones, phenyl dimethicones, phenyl trimethylsiloxydiphenylsiloxanes, diphenyl dimethicones, diphenyl methyldiphenyl trisiloxanes, 2-phenylethyl trimethylsiloxysilicates, trimethyl pentaphenyl trisiloxane, tetramethyl hexaphenyl trisiloxane.

Examples of other non-volatile oils which can be used in the compositions of the present invention include polar oils such as:

hydrocarbon-based plant oils with a high triglyceride content consisting of fatty acid esters of glycerol, the fatty acids of which may have varied chain lengths, these chains possibly being linear or branched, and saturated or unsaturated; these oils are especially wheat germ oil, corn oil, sunflower oil, karite butter, castor oil, sweet almond oil, macadamia oil, apricot oil, soybean oil, rapeseed oil, cottonseed oil, alfalfa oil, poppy oil, pumpkin oil, sesame seed oil, marrow oil, avocado oil, hazelnut oil, grape seed oil, blackcurrant seed oil, evening primrose oil, millet oil, barley oil, quinoa oil, olive oil, rye oil, safflower oil, candlenut oil, passion flower oil or musk rose oil; or caprylic/capric acid triglycerides, for instance those sold by the company Stearineries Dubois or those sold under the names Miglyol 810, 812 and 818 by the company Dynamit Nobel;

synthetic oils or esters of formula $R_5COOR_6$ in which $R_5$ represents a linear or branched higher fatty acid residue containing from 1 to 40 carbon atoms, including from 7 to 19 carbon atoms, and $R_6$ represents a branched hydrocarbon-based chain containing from 1 to 40 carbon atoms, including from 3 to 20 carbon atoms, with $R_6+R_7 \geq 10$, such as, for example, Purcellin oil (cetostearyl octanoate), isononyl isononanoate, $C_{12}$ to $C_{15}$ alkyl benzoate, isopropyl myristate, 2-ethylhexyl palmitate, and octanoates, decanoates or ricinoleates of alcohols or of polyalcohols; hydroxylated esters, for instance isostearyl lactate or diisostearyl malate; and pentaerythritol esters;

synthetic ethers containing from 10 to 40 carbon atoms; $C_8$ to $C_{26}$ fatty alcohols, for instance oleyl alcohol; and mixtures thereof.

The liquid fatty phase is present in the composition of the invention in an amount ranging from about 10% to about 90% by weight, such as from about 20% to about 80% by weight, such as from about 30% to about 70% by weight, all weights based on the weight of the composition as a whole.

Emulsifier

The cosmetic compositions of the present invention comprise at least one emulsifier chosen from an emulsifying silicone elastomer.

Emulsifying silicone elastomers suitable for use in the composition of the invention include, but are not limited to, Dimethicone/PEG-10/15 Crosspolymer commercially available as KSG-210 from Shin-Etsu, Dimethicone/Polyglycerin-3 Crosspolymer commercially available as KSG 710 from Shin-Etsu, Lauryl PEG-15 Dimethicone/ Vinyl Dimethicone Crosspolymer commercially available as KSG-31 from Shin-Etsu, and PEG-12 Dimethicone Crosspolymer, commercially available as DC 9011 from Dow Corning.

In one embodiment, the emulsifying silicone elastomer is Dimethicone/Polyglycerin-3 Crosspolymer.

The emulsifying silicone elastomer is generally present in the cosmetic composition of the present invention in an amount ranging from about 0.1% to about 10% by weight, such as from about 0.2% to about 7% by weight, such as from about 0.2% to about 5% by weight, all weights based on the weight of the composition as a whole.

Colorant

The cosmetic compositions of the present invention also contain at least one cosmetically acceptable colorant such as a pigment or dyestuff. Examples of suitable pigments include, but are not limited to, inorganic pigments, organic pigments, lakes, pearlescent pigments, irridescent or optically variable pigments, and mixtures thereof. A pigment should be understood to mean inorganic or organic, white or colored particles. Said pigments may optionally be surface-treated within the scope of the present invention but are not limited to treatments such as silicones, perfluorinated compounds, lecithin, and amino acids.

Representative examples of inorganic pigments useful in the present invention include those selected from the group consisting of rutile or anatase titanium dioxide, coded in the Color Index under the reference CI 77,891; black, yellow, red and brown iron oxides, coded under references CI 77,499, 77, 492 and, 77,491; manganese violet (CI 77,742); ultramarine blue (CI 77,007); chromium oxide (CI 77,288); chromium hydrate (CI 77,289); and ferric blue (CI 77,510) and mixtures thereof.

Representative examples of organic pigments and lakes useful in the present invention include, but are not limited to, D&C Red No. 19 (CI 45,170), D&C Red No. 9 (CI 15,585), D&C Red No. 21 (CI 45,380), D&C Orange No. 4 (CI 15,510), D&C Orange No. 5 (CI 45,370), D&C Red No. 27 (CI 45,410), D&C Red No. 13 (CI 15,630), D&C Red No. 7 (CI 15,850), D&C Red No. 6 (CI 15,850), D&C Yellow No. 5 (CI 19,140), D&C Red No. 36 (CI 12,085), D&C Orange No. 10 (CI 45,425), D&C Yellow No. 6 (CI 15,985), D&C Red No. 30 (CI 73,360), D&C Red No.3 (CI 45,430) and the dye or lakes based on cochineal carmine (CI 75,570) and mixtures thereof.

Representative examples of pearlescent pigments useful in the present invention include those selected from the group consisting of the white pearlescent pigments such as mica coated with titanium oxide, mica coated with titanium dioxide, bismuth oxychloride, titanium oxychloride, colored pearlescent pigments such as titanium mica with iron oxides, titanium mica with ferric blue, chromium oxide and the like, titanium mica with an organic pigment of the above-mentioned type as well as those based on bismuth oxychloride and mixtures thereof.

The precise amount and type of colorant employed in the compositions of the present invention will depend on the color, intensity and use of the cosmetic composition and, as a result, will be determined by those skilled in the art of cosmetic formulation.

The cosmetic compositions of the present invention also contain water in an amount ranging from about 1% to about 95% by weight, such as from about 5% to about 90% by weight, such as from about 10% to about 85% by weight, all weights based on the weight of the composition as a whole.

Optional Ingredients
Film Forming Resins

In an effort to enhance the long wear properties of the composition, it may be desirable to include a film forming resin in the composition of the present invention. Suitable film forming resins include, but are not limited to, propylphenylsilsesquioxane resins and silicone acrylate copolymers resins.

Silsesquioxane resins are a specific form of film forming silicone resins. Silicone resins are crosslinked organopolysiloxanes which are solid at room temperature and generally soluble in organic solvents. When they are soluble in volatile solvents, silicone resins are capable of forming a film once the solvent has evaporated. Furthermore, if the solvent dissolving the silicone resin is absorbed on the substrate onto which it is applied, the silicone resin which remains on the substrate may also form a film.

The compositions of the present invention comprise propylphenylsilsesquioxane resins, which have been disclosed in patent publications WO2005/090444, published on Sep. 29, 2005; US20040180011, published on Sep. 16, 2004; and US20040156806, published on Aug. 12, 2004, the entire contents of each of which are hereby incorporated by reference.

The propylphenylsilsesquioxane resin comprises at least about 70 mole % of propyl siloxy units ($C_3H_7SiO_{3/2}$), based on the total mole % siloxy units of the resin, and at most about 30 mole % of phenyl siloxy units ($C_6H_5SiO_{3/2}$), based on the total mole % siloxy units of the resin.

The propylphenylsilsesquioxane resin will have a weight average molecular weight of from about 2,000 to about 30,000, such as from about 3,000 to about 20,000.

The propylphenylsilsesquioxane resins preferably soften in the range of from about 30° C. to about 100° C., such as from about 30° C. to about 80° C., and such as from about 40° C. to about 70° C., as determined by DIN 53180 "Softening Point of Resins".

The mole % of propyl siloxy units to phenyl siloxy units can be adjusted depending on an intended application. As such, it is possible to have propylphenylsilsesquioxane resins having a mole % propyl siloxy units:phenyl siloxy units ranging from about 70:30 to about 100:0, such as 70:30; 80:20; 90:10; and 100:0; and subranges therebetween. When the mole % of the propyl siloxy units is about 100 mole %, the propylphenylsilsesquioxane resin is referred to as a propylsilsesquioxane resin.

A suitable example of a propylphenylsilsesquioxane resin for use in cosmetic compositions of the present invention includes, but is not limited to, a propylsilsesquioxane resin commercially available from Dow-Corning under the tradename DC 670 Fluid.

The propylphenylsilsesquioxane film forming resin may be present in an amount ranging from about 0.5% to about 50% by weight, such as from about 1% to about 40% by weight, such as from about 2% to about 30% by weight, such as from about 3% to about 20% by weight, and such as from about 4% to about 10% by weight, all weights based on the weight of the composition as a whole.

Silicone acrylate copolymer resins are another specific form of film forming silicone resins. They are available as silicone acrylate copolymers with a (meth)acrylate backbone grafted with a silicone chain or as a silicone backbone grafted with a (meth)acrylate, or as a silicone acrylate dendrimer.

Suitable silicone acrylate copolymer resins include, but are not limited to, those described in co-pending application Ser. No. 11/584,994, also published as US20070093619, the entire contents of which are hereby incorporated by reference. Examples of silicone acrylate copolymer resins include, but are not limited to, those commercially available from Shin-Etsu as KP-545, KP-561 and KP-562 and those commercially available from 3M as SA-70-5 IBMMF and VS70 IBM.

Silicone acrylate dendrimers, such as those described and claimed in U.S. Pat. No. 6,280,748, the entire contents of which is hereby incorporated by reference, are preferred for use in the composition of the present invention. The silicone acrylate dendrimer is comprised of a vinyl polymer having a carbosiloxane dendrimer structure in its side molecular chain. It is characterized by a vinyl-type polymer which has in its side molecular chain a carbosiloxane dendrimer structure. The term "carbosiloxane dendrimer structure" is a structure with high-molecular-weight groups branched with high regularity in a radial direction from a single core.

The vinyl polymer backbone is formed from a vinyl-type monomer which contains a radical polymerizable vinyl group. In its broadest definition, there are no particular limitations with regards to the type of such a monomer. A particularly preferred vinyl polymer is a (meth)acrylate.

The number-average molecular weight of the silicone acrylate dendrimers for use in the composition of the present invention ranges from about 3,000 to about 2,000,000, such as from about 5,000 to about 800,000.

Particularly preferred silicone acrylate dendrimers for use in the composition of the present invention are available from Dow Corning as FA-4001 CM silicone acrylate, a 30% solution in cyclomethicone, and as FA-4002 ID silicone acrylate, a 40% solution in isododecane, under the INCI name of Acrylates/Polytrimethylsiloxymethacrylate Copolymer.

The silicone acrylate copolymer resin may be present in the composition of the invention in an amount ranging from about 0.5% to about 20% by weight, such as from about 0.7% to about 15% by weight, such as from about 1% to about 10% by weight, all weights based on the weight of the composition as a whole.

Waxes

In some embodiments, it may be desirable to formulate cosmetic compositions in accordance with the present invention with other waxes in addition to the propylsilsesquioxane wax. Suitable waxes are those generally used in cosmetics and dermatology. Examples thereof include, but are not limited to, those of natural origin such as beeswax, carnauba wax, candelilla wax, ouricury wax, Japan wax, cork fiber wax, sugar cane wax, paraffin wax, lignite wax, microcrystalline waxes, lanolin wax, montan wax, ozokerites and hydrogenated oils such as hydrogenated jojoba oil. Examples of suitable synthetic waxes include, but are not limited to, polyethylene waxes derived from the polymerization of ethylene, waxes obtained by Fischer-Tropsch synthesis, fatty acid esters and glycerides that are solid at 40° C., for example, at above 55° C., silicone waxes such as alkyl- and alkoxy-poly (di)methylsiloxanes and/or poly(di)methyl-siloxane esters that are solid at 40° C., for example, at above 55° C.

The additional waxes may be present in the composition of the present invention in an amount ranging from about 0.5% to about 20%, such as from about 1% to about 10% by weight, all weights based on the weight of the composition as a whole.

Gelling Agents

The compositions of the invention may also be optionally gelled with an oil-phase gelling agent. The gelling agent increases the liquid fatty phase viscosity and leads to a solid or flowable composition when introduced in said fatty phase. The gelling agent does not encompass waxes, in the sense that it is not waxy. The at least one gelling agent may be chosen from gelling agents in polymeric form and gelling agents in mineral form. The gelling agent may be chosen from agents that gel via chemical cross-linking and agents that gel via physical cross-linking.

Modified clays may be used as gelling agents, examples of which include, but are not limited to, hectorites modified with an ammonium chloride of a $C_{10}$ to $C_{22}$ fatty acid, such as hectorite modified with distearyldimethylammonium chloride, also known as quaternium-18 bentonite, such as the products sold or made under the names Bentone 34 by the company Rheox, Claytone XL, Claytone 34 and Claytone 40 sold or made by the company Southern Clay, the modified clays known under the name quaternium-18 benzalkonium bentonites and sold or made under the names Claytone HT, Claytone GR and Claytone PS by the company Southern Clay, the clays modified with stearyldimethylbenzoylammonium chloride, known as stearalkonium bentonites, such as the products sold or made under the names Claytone APA and Claytone AF by the company Southern Clay, and Baragel 24 sold or made by the company Rheox.

Other mineral gelling agents, which can be used in the invention, include silica, such as fumed silica. The fumed silica may have a particle size, which may be nanometric to micrometric, for example ranging from 5 nm to 200 nm.

The fumed silicas may be obtained by high-temperature hydrolysis of a volatile silicon compound in a hydrogen-oxygen flame, producing a finely divided silica. This process makes it possible to obtain hydrophilic silicas that have a large number of silanol groups at their surface. Such hydrophilic silicas are sold or made, for example, under the names "Aerosil 130®", "Aerosil 200®", "Aerosil 255®", "Aerosil 300®" and "Aerosil 380®" by the company Degussa, and "CAB-O-SIL HS-5®", "CAB-O-SIL EH-5®", "CAB-O-SIL LM-130", "CAB-O-SIL MS-55®" and "CAB-O-SIL M-5®" by the company Cabot.

It is thus possible to chemically modify the surface of the hydrophilic silica by chemical reaction, producing a reduction in the number of silanol groups. The silanol groups can be replaced, for example, with hydrophobic groups: this then gives a hydrophobic silica. The hydrophobic groups may be: trimethylsiloxyl groups, which are obtained in particular by treating fumed silica in the presence of hexamethyldisilazane. Silicas thus treated are known as "silica silylate" according to the CTFA dictionary (6th edition, 1995). They are sold or made, for example, under the references "Aerosil R812" by the company Degussa and "CAB-o-SIL TS-530" by the company Cabot; dimethylsilyloxyl or polydimethylsiloxane groups, which are obtained in particular by treating fumed silica in the presence of polydimethylsiloxane or dimethyldichlorosilane. Silicas thus treated are known as "silica dimethyl silylate" according to the CTFA dictionary (6th edition, 1995). They are sold or made, for example, under the references "Aerosil R972" and "Aerosil R974®" by the company Degussa, and "CAB-O-SIL TS-610®" and "CAB-O-SIL TS-720" by the company Cabot; groups derived from reacting fumed silica with silane alkoxides or siloxanes. These treated silicas are, for example, the products sold or made under the reference "Aerosil R805®" by the company Degussa.

According to the invention, hydrophobic silica, such as fumed silica, may be used as a lipophilic gelling agent. The use of fumed silica makes it possible to obtain a translucent or even transparent composition, in particular in the form of a stick, which does not exude, in the absence of opacifying particles such as waxes, fillers and pigments (including nacres).

The at least one lipophilic gelling agent can allow the exudation of the composition to be limited and can allow its stability to be increased, while at the same time conserving the composition's glossy appearance, which is not possible with waxes such as those used conventionally in cosmetics and dermatology.

The at least one gelling agent, if used, will typically be present in the composition of the invention in an amount ranging from about 0.1% to about 20% by weight, such as from about 0.1% to about 15% by weight, such as from about 0.1% to about 10% by weight, all weights based on the weight of the composition as a whole.

Non-Emulsifying Silicone Elastomers

The compositions of the present invention may also contain non-emulsifying silicone elastomers.

The term "non-emulsifying" defines silicone elastomers which do not contain a hydrophilic chain, such as polyoxyalkylene or polyglycerolated units.

The non-emulsifying silicone elastomer may be conveyed in the form of a gel consisting of an elastomeric organopolysiloxane included in at least one hydrocarbon-based oil and/or one silicone oil. The elastomeric crosslinked organopolysiloxanes may also be in powder form.

Suitable non-emulsifying silicone elastomers for use in the composition of the present invention include, but are not limited to, those sold under the names "DC 9040", "DC 9041", "DC 9509", "DC 9505" and "DC 9506" available from Dow Corning, and KSG-6, KSG-8, KSG-10, KSG-14, KSG-15, and KSG-16 available from Shin-Etsu; SFE-168 and SFE-839 available from GE Silicones; and Gransil SR-SYC available from Grant Industries.

The non-emulsifying silicone elastomer may also be in the form of an elastomeric crosslinked organopolysiloxane powder coated with silicone resin, especially with silsesquioxane resin, as described, for example, in patent U.S. Pat. No. 5,538,793, the entire content of which is herein incorporated by reference. Such elastomers are sold under the names "KSP-100", "KSP-101", "KSP-102", "KSP-103", "KSP-104" and "KSP-105" by the company Shin-Etsu.

Other non-emulsifying silicone elastomer in the form of powders include hybrid silicone powders functionalized with fluoroalkyl groups, available as "KSP-200" from the company Shin-Etsu; and hybrid silicone powders functionalized with phenyl groups, available as "KSP-300" from the company Shin-Etsu.

Additional non-emulsifying silicone elastomers in the form of powders include cured silicone powder coated with microfine particles. These particles are described in U.S. Pat. No. 5,492,945, U.S. Pat. No. 5,756,568 and U.S. Pat. No. 5,945,471, the entire contents of which are hereby incorporated by reference. Suitable cured silicone powder coated with microfine particles include, but are not limited to DC9701, available from Dow Corning.

The non-emulsifying silicone elastomer may be present in the cosmetic composition of the invention in an amount ranging from about 0.1% to about 50% by weight, such as from about 0.1% to about 40% by weight; such as from about 0.1% to about 30% by weight; such as from about 0.1% to about 20% by weight; such as from about 0.5% to about 10% by weight; such as from 3% to 10% by weight, all weights based on the weight of the composition as a whole.

Plasticizers are organic compounds added to a high molecular weight polymer both to facilitate processing and to increase the flexibility and toughness of the final product by internal modification of the polymer molecule. Examples of plasticizers include, but are not limited to, oils, cellulose esters, phthalate esters, adipate esters, sebacate esters, tricresyl phosphate, castor oil, glycol ethers, benzyl alcohol, triethyl citrate, and propylene carbonate.

It has been surprisingly discovered, however, that the present invention does not require the use of a plasticizer. Consequently, in a preferred embodiment, the composition is substantially free of a plasticizer, i.e., it contains less than about 5% by weight, such as less than about 4% by weight, such as less than about 3% by weight, such as less than about 2% by weight, such as less than about 1% by weight, based on the total weight of the composition, of a plasticizer.

Representative examples of preservatives include alkyl para-hydroxybenzoates, wherein the alkyl radical has from 1, 2, 3, 4, 5 or 6 carbon atoms and preferably from 1 to 4 carbon atoms e.g., methyl para-hydroxybenzoate (methylparaben), ethyl para-hydroxybenzoate (ethylparaben), propyl para-hydroxybenzoate (propylparaben), butyl para-hydroxybenzoate (butylparaben) and isobutyl para-hydroxybenzoate (isobutylparaben). Mixtures of preservatives may certainly be used, e.g., the mixture of methyl-paraben, ethylparaben, propylparaben and butylparaben sold under the name Nipastat by Nipa, and the mixture of phenoxyethanol, methylparaben, ethylparaben, propylparaben and butylparaben sold under the name Phenonip, also by Nipa. These preservatives may be present in an amount ranging from about 0.01% to about 10% by weight, such as from 0.5% to about 5% by weight, and such as from about 0.8% to about 3% by weight, all weights based on the weight of the composition as a whole.

Fillers that may be used in the compositions of the invention include, for example, silica powder; talc; polyamide particles and especially those sold under the name Orgasol by the company Atochem; polyethylene powders; microspheres based on acrylic copolymers, such as those based on ethylene glycol dimethacrylate/lauryl methacrylate copolymer sold by the company Dow Corning under the name Polytrap; expanded powders such as hollow microspheres and especially the microspheres sold under the name Expancel by the company Kemanord Plast or under the name Micropearl F 80 ED by the company Matsumoto; powders of natural organic materials such as crosslinked or noncrosslinked corn starch, wheat starch or rice starch, such as the powders of starch crosslinked with octenyl succinate anhydride, sold under the name Dry-Flo by the company National Starch; silicone resin microbeads such as those sold under the name Tospearl by the company Toshiba Silicone; clays (bentone, laponite, saponite, etc.); and mixtures thereof.

The fillers may be present in the composition of the invention in an amount ranging from about 0.1% to about 50% by weight, such as from 0.5% to about 30% by weight, and such as from about 1% to about 20% by weight, all weights based on the weight of the composition as a whole.

The compositions of the present invention may further comprise a safe and effective amount of at least one active ingredient or pharmaceutically acceptable salt thereof. The term "safe and effective amount" as used herein, means an amount sufficient to modify the condition to be treated or to deliver the desired skin benefit, while at the same time avoiding serious side effects, at a reasonable benefit to risk ratio within the scope of sound medical judgment. What is a safe and effective amount of the active ingredient will vary with the specific active agent, the ability of the active agent to penetrate through the skin, the age, health and skin condition of the user, and other like factors. Typically, the active ingredient may be present in an amount ranging from about 0.01% to about 20% by weight, such as from about 0.1% to about 10% by weight, and such as from about 0.5% to about 5% by weight, all weights based on the weight of the composition as a whole.

The active ingredients useful herein can be categorized by their therapeutic benefit or their postulated mode of action. However, it is to be understood that the active ingredients useful herein can in some instances provide more than one therapeutic benefit or operate via more than one mode of action. Therefore, classifications herein are made for the sake of convenience and are not intended to limit the active ingredient to that particular application or applications listed. Also, pharmaceutically acceptable salts of these active ingredients are useful herein. The following active ingredients are useful in the compositions of the present invention.

The cosmetic compositions of the present invention may also contain sunscreens, which are chemical absorbers that actually absorb harmful ultraviolet radiation. It is well known that chemical absorbers are classified, depending on the type of radiation they protect against, as either UV-A or UV-B absorbers. UV-A absorbers generally absorb radiation in the 320 to 400 nm region of the ultraviolet spectrum. UV-A absorbers include anthranilates, benzophenones, and dibenzoyl methanes. UV-B absorbers generally absorb radiation in the 280 to 320 nm region of the ultraviolet spectrum. UV-B absorbers include p-aminobenzoic acid derivatives, camphor derivatives, cinnamates, and salicylates.

The sunscreens useful in the present invention typically comprise chemical absorbers, but may also comprise physical blockers. Exemplary sunscreens which may be formulated into the compositions of the present invention are chemical absorbers such as p-aminobenzoic acid derivatives, anthranilates, benzophenones, camphor derivatives, cinnamic derivatives, dibenzoyl methanes (such as avobenzone also known as Parsol 1789), diphenylacrylate derivatives, salicylic derivatives, triazine derivatives, benzimidazole compounds, bis-benzoazolyl derivatives, methylene bis-(hydroxyphenylbenzotriazole) compounds, the sunscreen polymers and silicones, or mixtures thereof. Also exemplary of the sunscreens which may be formulated into the compositions of this invention are physical blockers such as cerium oxides, chromium oxides, cobalt oxides, iron oxides, red petrolatum, silicone-treated titanium dioxide, titanium dioxide, zinc oxide, and/or zirconium oxide, or mixtures thereof.

Examples of suitable sunscreens include, but are not limited to: aminobenzoic acid, amyldimethyl PABA, cinoxate, diethanolamine p-methoxycinnamate, digalloyl trioleate, dioxybenzone, 2-ethoxyethyl p-methoxycinnamate, ethyl 4-bis(hydroxypropyl)aminobenzoate, 2-ethylhexyl-2-cyano-3,3-diphenylacrylate, ethylhexyl p-methoxycinnamate, 2-ethylhexyl salicylate, glyceryl aminobenzoate, homomenthyl salicylate, homosalate, 3-imidazol-4-ylacrylic acid and ethyl ester, methyl anthranilate, octyldimethyl PABA, 2-phenylbenzimidazole-5-sulfonic acid and salts, red petrolatum, sulisobenzone, titanium dioxide, triethanolamine salicylate, N,N,N-trimethyl-4-(2-oxoborn-3-ylidene methyl)anillinium methyl sulfate, and mixtures thereof.

The sunscreens may be present in the composition of the invention in an amount ranging from greater than about 0 to about 30% by weight, based on the weight of the composition as a whole.

The present invention is further described in terms of the following non-limiting examples. Unless otherwise indicated, all parts and percentages are on a weight-by-weight percentage basis.

EXAMPLES

Two foundations were prepared containing the below-disclosed ingredients.

| Phase | Trade Name | INCI Name | Ex. 1 Inventive w/w % | Ex. 2 Comparative w/w % |
|---|---|---|---|---|
| A1 | DC-245 | Cyclopentasiloxane | 24.0 | 24.0 |
| A1 | NA | Propylsilsesquioxane wax substituted with alkyl units having at least 30 carbons (Dow Corning) | 4.0 | 0 |
| A1 | NA | Propylsilsesquioxane wax substituted with alkyl units having 28 carbons (Dow Corning) | 0 | 4.0 |
| A2 | DC670 | Propylsilsesquioxane resin | 12.0 | 12.0 |
| A2 | ABIL EM 90 | Cetyl PEG/PPG-10/1 Dimethicone | 2.0 | 2.0 |
| B1 | | Pigment grind 61 | 10.0 | 10.0 |
| B2 | KSG 710 | Dimethicone and Dimethicone/Polyglycerin-3 Crosspolymer | 6.0 | 6.0 |
| B3 | SUNSPHERE H 51 | Silica | 3.0 | 3.0 |
| B3 | ORGASOL 2002 | Nylon-12 | 1.0 | 1.0 |
| C | | Glycerin | 5.0 | 5.0 |
| C | | Phenoxyethanol | 0.4 | 0.4 |
| C | | Deionized Water | 32.6 | 32.6 |
| | | TOTAL | 100.0 | 100.0 |

| PIGMENT GRIND 61 | | Grams | Grams |
|---|---|---|---|
| Titanium Dioxide | Titanium Dioxide (and) Disodium Stearoyl Glutamate (and) Aluminum Hydroxide | 10.42 | 10.42 |
| Iron Oxide Yellow | Iron oxides (and) Disodium Stearoyl Glutamate (and) Aluminum Hydroxide | 1.03 | 1.03 |
| Iron Oxide Red | Iron Oxides (and) Disodium Stearoyl Glutamate (and) Aluminum Hydroxide | 0.34 | 0.34 |
| Iron Oxide Black | Iron Oxides (and) Disodium Stearoyl Glutamate (and) Aluminum Hydroxide | 0.21 | 0.21 |
| | Cyclopentasiloxane | 3.75 | 3.75 |

The foundation of the inventive composition was found to be stable, transfer resistant, comfortable and smooth feeling, whereas the foundation of the comparative composition was unstable and developed a grainy texture.

Preparation of Examples

Phase A1 was mixed in main beaker at 85° C. until the propylsilsesquioxane wax was fully dissolved.

Phase A2 was added with mixing to Phase A1 while maintaining temperature at 85° C.

Previously prepared Phase B1 phase was added to the main beaker with mixing at 85° C.

Phases B2 and B3 were added to the main beaker at 85° C. until completely mixed.

Phase C was prepared at 85° C. in a separate beaker and mixed until fully dissolved.

Phase C was slowly poured into the main beaker (phases A and B) at high shear.

The mixture was homogenized, and then cooled to room temperature.

Example 3

Inventive Composition: Foundation

| Phase | Trade Name | INCI Name | Ex. 3 w/w % |
|---|---|---|---|
| A1 | DC-245 | Cyclopentasiloxane | 21.0 |
| A1 | NA | Propylsilsesquioxane wax substituted with alkyl units having at least 30 carbons (Dow Corning) | 4.0 |
| A2 | DC FA 4002 | Acrylates/Polytrimethylsiloxymethacrylate Copolymer | 15.0 |
| A2 | ABIL EM 90 | Cetyl PEG/PPG-10/1 Dimethicone | 2.0 |
| B1 | | Pigment Grind | 10.0 |
| B2 | KSG 710 | Dimethicone and Dimethicone/Polyglycerin-3 Crosspolymer | 6.0 |
| B3 | SUNSPHERE H 51 | Silica | 3.0 |
| B3 | ORGASOL 2002 | Nylon-12 | 1.0 |
| C1 | | Glycerin | 5.0 |
| C1 | | Phenoxyethanol | 0.4 |
| C1 | | DI Water | 32.6 |
| | | TOTAL | 100.0 |

| PIGMENT GRIND | | Grams |
|---|---|---|
| Titanium Dioxide | Titanium Dioxide (and) Disodium Stearoyl Glutamate (and) Aluminum Hydroxide | 10.42 |

-continued

| | | |
|---|---|---|
| Iron Oxide - Yellow | Iron Oxides (and) Disodium Stearoyl Glutamate (and) Aluminum Hydroxide | 1.03 |
| Iron Oxide - Red | Iron Oxides (and) Disodium Stearoyl Glutamate (and) Aluminum Hydroxide | 0.34 |
| Iron Oxide - Black | Iron Oxides (and) Disodium Stearoyl Glutamate (and) Aluminum Hydroxide | 0.21 |
| | Cyclopentasiloxane | 3.75 |

The inventive composition of example 3 was also found to be stable, transfer resistant, comfortable and smooth feeling.

Example 4

Inventive Foundation

| Phase | Trade Name | INCI Name | w/w % |
|---|---|---|---|
| A1 | DC-245 | Cyclopentasiloxane | 14.165 |
| | Isododecane | Isododecane | 5.000 |
| A1 | Silicone wax | Propylsilsesquioxane wax substituted with alkyl units having at least 30 carbons (Dow Corning) | 4.000 |
| | DC670 | Polypropylsilsesquioxane (and) Cyclopentasiloxane | 12.000 |
| A2 | PEG-10 Dimethicone | PEG-10 Dimethicone | 1.950 |
| | Pigment Paste | White TiO$_2$ & Disodium Stearoyl Glutamate & Aluminum Hydroxide | 7.820 |
| | | Cyclopentasiloxane | 3.016 |
| | | PEG-10 Dimethicone | 0.335 |
| | Pigment Paste | Yellow Iron Oxides & Disodium Stearoyl Glutamate & Aluminum Hydroxide | 1.460 |
| | | Cyclopentasiloxane | 1.115 |
| | | PEG-10 Dimethicone | 0.080 |
| | Pigment Paste | Red Iron Oxides & Disodium Stearoyl Glutamate & Aluminum Hydroxide | 0.530 |
| | | Cyclopentasiloxane | 0.204 |
| | | PEG-10 Dimethicone | 0.023 |
| | Pigment Paste | Black Iron Oxides & Disodium Stearyl Glutamate & Aluminum Hydroxide | 0.200 |
| | | Cyclopentasiloxane | 0.125 |
| | | PEG-10 Dimethicone | 0.009 |
| A4 | Bentone | Bentone | 0.60 |
| A5 | SUNSPHERE H 51 | Silica | 3.00 |
| A5 | ORGASOL 2002 | Nylon-12 | 1.00 |
| A5 | EXPANCEL 551 DE 40 D42 | Acrylate Copolymer | 0.200 |
| A6 | KSG 710 | Dimethicone and Dimethicone/Polyglycerin-3 Crosspolymer | 6.000 |
| B1 | | DI Water | 31.868 |
| | | Disodium EDTA | 0.200 |
| | | Sodium Chloride | 1.000 |
| | | Glycerin | 3.000 |
| | | Preservatives | 1.100 |
| | | TOTAL | 100.000 |

This foundation exhibited improved stability.

It is to be understood that the foregoing describes preferred embodiments of the invention and that modifications may be made therein without departing from the spirit or scope of the invention as set forth in the claims.

What is claimed is:

1. A cosmetic composition for application to the skin comprising:
   a) at least one propylsilsesquioxane wax substituted with alkyl units having at least 30 carbons which is present in the composition in an amount ranging from about 3% to about 10% by weight, based on the weight of the composition as a whole;
   b) a liquid fatty phase comprising at least one silicone oil comprising cyclopentasiloxane, dimethicone or a combination thereof;
   c) at least one emulsifier chosen from an emulsifying silicone elastomer comprising dimethicone and dimethicone/polyglycerin-3 crosspolymer, cetyl PEG/PPG-10/1 dimethicone, or a combination thereof, wherein the emulsifier is present in an amount ranging from about 0.1% to about 10% by weight, based on the weight of the composition as a whole;
   d) at least one colorant;
   e) water; and
   f) at least one film forming resin chosen from a propylphenylsilsesquioxane resin having a molecular weight of from about 2,000 to about 30,000 and comprising at least about 70 mole % propyl siloxy units ($C_3H_7SiO_{3/2}$) based on the total mole % siloxy units of the resin, and from greater than 0% to about 30 mole % phenyl siloxy units ($C_6H_5SiO_{3/2}$) based on the total mole % siloxy units of the resin, and a propylsilsesquioxane resin having a molecular weight of from about 2,000 to about 30,000.

2. The composition of claim 1, wherein (b) is present in the composition in an amount ranging from about 10% to about 90% by weight, based on the weight of the composition as a whole.

3. The composition of claim 1, wherein (b) is present in the composition in an amount ranging from about 30% to about 70% by weight, based on the weight of the composition as a whole.

4. The composition of claim 1, wherein (c) is present in the composition in an amount ranging from about 0.2% to about 7% by weight, based on the weight of the composition as a whole.

5. The composition of claim 1, wherein (f) is a propylphenylsilsesquioxane resin having a molecular weight of from about 3,000 to about 20,000.

6. The composition of claim 1, wherein (f) is a propylsilsesquioxane resin.

7. The composition of claim 1, wherein the composition is substantially free of a plasticizer.

8. The composition of claim 1, wherein the at least one silicone oil comprises cycopentasiloxane and dimethicone.

9. The composition of claim 1, wherein the at least one silicone oil comprises cycopentasiloxane.

10. The composition of claim 1, wherein the at least one silicone oil comprises dimethicone.

11. The composition of claim 10, further comprising isododecane.

12. The composition of claim 1, further comprising silica.

13. The composition of claim 1, further comprising nylon-12.

14. The composition of claim 1, further comprising PEG-10 dimethicone.

15. A method of making up skin comprising applying onto the skin a composition containing:
   a) at least one propylsilsesquioxane wax substituted with alkyl units having at least 30 carbons which is present in the composition in an amount ranging from about 3% to about 10% by weight, based on the weight of the composition as a whole;
   b) a liquid fatty phase comprising at least one silicone oil comprising cyclopentasiloxane, dimethicone or a combination thereof;

c) at least one emulsifier chosen from an emulsifying silicone elastomer comprising dimethicone and dimethicone/polyglycerin-3 crosspolymer, cetyl PEG/PPG-10/1 dimethicone, or a combination thereof, wherein the emulsifier is present in an amount ranging from about 0.1% to about 10% by weight, based on the weight of the composition as a whole;
d) at least one colorant;
e) water; and
f) at least one film forming resin chosen from a propylphenylsilsesquioxane resin having a molecular weight of from about 2,000 to about 30,000 and comprising at least about 70 mole % propyl siloxy units ($C_3H_7SiO_{3/2}$) based on the total mole % siloxy units of resin, and from greater than 0% to about 30 mole % phenyl siloxy units ($C_6H_5SiO_{3/2}$) based on the total mole % siloxy units of the resin, and a propylsilsesquioxane resin having a molecular weight of from about 2,000 to about 30,000.

16. The method of claim 15, wherein (b) is present in the composition in an amount ranging from about 10% to about 90% by weight, based on the weight of the composition as a whole.

17. The method of claim 15, wherein (b) is present in the composition in an amount ranging from about 30% to about 70% by weight, based on the weight of the composition as a whole.

18. The method of claim 15, wherein (c) is present in the composition in an amount ranging from about 0.2% to about 7% by weight, based on the weight of the composition as a whole.

19. The method of claim 15, wherein (f) is a propylphenylsilsesquioxane resin having a molecular weight of from about 3,000 to about 20,000.

20. The method of claim 15, wherein (f) is a propylsilsesquioxane resin.

21. The method of claim 15, wherein the composition is substantially free of a plasticizer.

22. The method of claim 15, wherein the at least one silicone oil comprises cycopentasiloxane and dimethicone.

23. The method of claim 15, wherein the at least one silicone oil comprises cycopentasiloxane.

24. The method of claim 15, wherein the at least one silicone oil comprises dimethicone.

25. The method of claim 24, further comprising isododecane.

26. The method of claim 15, further comprising silica.

27. The method of claim 15, further comprising nylon-12.

28. The method of claim 15, further comprising PEG-10 dimethicone.

* * * * *

UNITED STATES PATENT AND TRADEMARK OFFICE
CERTIFICATE OF CORRECTION

PATENT NO.       : 9,089,503 B2
APPLICATION NO.  : 12/131256
DATED            : July 28, 2015
INVENTOR(S)      : Hy Si Bui, Susan Halpern and Mohamed Kanji Page 1 of 1

It is certified that error appears in the above-identified patent and that said Letters Patent is hereby corrected as shown below:

In the Claims

Column 13, line 67, "30carbons" should read --30 carbons--.
Column 14, line 21, "30mole" should read --30 mole--.
Column 14, line 46, "cycopentasiloxane" should read --cyclopentasiloxane--.
Column 14, line 48, "cycopentasiloxane" should read --cyclopentasiloxane--.
Column 14, line 61, "30carbons" should read --30 carbons--.
Column 15, line 12, "2,000to" should read --2,000 to--; "30,000and" should read --30,000 and--.
Column 15, line 13, "70mole" should read --70 mole--.
Column 15, line 15, "30mole" should read --30 mole--.
Column 15, line 18, "2,000to" should read --2,000 to--.
Column 16, line 7, "3,000to" should read --3,000 to--.
Column 16, line 13, "cycopentasiloxane" should read --cyclopentasiloxane--.
Column 16, line 15, "cycopentasiloxane" should read --cyclopentasiloxane--.

Signed and Sealed this
Fifteenth Day of December, 2015

Michelle K. Lee
*Director of the United States Patent and Trademark Office*